(12) United States Patent
Deng et al.

(10) Patent No.: US 12,702,275 B2
(45) Date of Patent: Aug. 11, 2026

(54) ENDOSCOPIC CAMERA COUPLER

(71) Applicant: Stryker Corporation, Kalamazoo, MI (US)

(72) Inventors: Wenjie Deng, San Jose, CA (US); William Huei Liang Chang, Milpitas, CA (US); Michelle Sun, San Jose, CA (US)

(73) Assignee: Stryker Corporation, Portage, MI (US)

( * ) Notice: Subject to any disclaimer, the term of this patent is extended or adjusted under 35 U.S.C. 154(b) by 278 days.

(21) Appl. No.: 18/512,003

(22) Filed: Nov. 16, 2023

(65) Prior Publication Data

US 2024/0164621 A1 May 23, 2024

Related U.S. Application Data

(60) Provisional application No. 63/384,407, filed on Nov. 18, 2022.

(51) Int. Cl.
*A61B 1/00* (2006.01)
*A61B 1/04* (2006.01)

(52) U.S. Cl.
CPC ...... *A61B 1/00126* (2013.01); *A61B 1/00042* (2022.02); *A61B 1/00105* (2013.01);
(Continued)

(58) Field of Classification Search
CPC ............ A61B 1/00042; A61B 1/00101; A61B 1/00105; A61B 1/00128; A61B 1/00188;
(Continued)

(56) References Cited

U.S. PATENT DOCUMENTS 4,249,799 A 2/1981 Iglesias
5,205,280 A 4/1993 Dennison, Jr.
(Continued)

FOREIGN PATENT DOCUMENTS

CN 108209848 A 6/2018
CN 109938678 A 6/2019
(Continued)

OTHER PUBLICATIONS

International Preliminary Report on Patentability dated Apr. 29, 2025, directed to International Application No. PCT/US2023/080096, 8 pages.
(Continued)

*Primary Examiner* — Aaron B Fairchild
(74) *Attorney, Agent, or Firm* — Morrison & Foerster LLP

(57) ABSTRACT

A coupler for coupling an endoscope to a camera head includes a base configured to mount to the camera head and to receive an eyepiece of the endoscope; a clamp for clamping the eyepiece in the base, the clamp configured to move laterally relative to a longitudinal axis of the coupler between a clamping position and non-clamping position; at least one clamping arm rotatably connected to the clamp and comprising a pin that moves in a slot of the base, wherein when the clamp moves laterally toward the clamping position, movement of the pin in the slot causes the at least one clamping arm to rotate into engagement with the eyepiece; and a button for pressing by a user to move the clamp from the clamping position to the non-clamping position.

19 Claims, 12 Drawing Sheets

(52) U.S. Cl.
CPC ...... *A61B 1/00137* (2013.01); *A61B 1/00188* (2013.01); *A61B 1/042* (2013.01)

(58) Field of Classification Search
CPC . A61B 1/042; A61B 1/00121; A61B 1/00126; A61B 1/00131; A61B 1/00137
USPC .......................................................... 600/112
See application file for complete search history.

(56) References Cited

U.S. PATENT DOCUMENTS

| | | | | |
|---|---|---|---|---|
| 5,591,119 | A * | 1/1997 | Adair | A61B 46/10 600/122 |
| 5,707,340 | A | 1/1998 | Hipp et al. | |
| 5,924,978 | A | 7/1999 | Koeda et al. | |
| D676,387 | S | 2/2013 | Kennedy et al. | |
| 8,708,891 | B2 | 4/2014 | Sjostrom et al. | |
| 2006/0229495 | A1 * | 10/2006 | Frith | A61B 1/00128 600/112 |
| 2011/0295071 | A1 * | 12/2011 | Sjostrom | A61B 1/00121 600/166 |
| 2015/0112137 | A1 * | 4/2015 | Hogrefe | A61B 1/00188 600/112 |
| 2019/0374095 | A1 | 12/2019 | Lord et al. | |
| 2020/0170487 | A1 | 6/2020 | Mattes et al. | |
| 2020/0367728 | A1 * | 11/2020 | Boysen | A61B 1/00126 |
| 2021/0212555 | A1 | 7/2021 | Pang et al. | |
| 2021/0282629 | A1 | 9/2021 | Taniguchi | |

FOREIGN PATENT DOCUMENTS

| | | | |
|---|---|---|---|
| CN | 110037645 | A | 7/2019 |
| CN | 210055942 | U | 2/2020 |
| CN | 210077606 | U | 2/2020 |
| CN | 210077607 | U | 2/2020 |
| CN | 111568339 | A | 8/2020 |
| CN | 113281895 | A | 8/2021 |
| DE | 3118990 | A1 | 12/1982 |
| JP | H11337846 | A | 12/1999 |
| WO | 2022/003569 | A1 | 1/2022 |

OTHER PUBLICATIONS

International Search Report and Written Opinion mailed Feb. 12, 2024, directed to International Application No. PCT/US2023/080096, 12 pages.

Lighthouse Optics. (Aug. 10, 2020) “Autoclavable Video Adaptor,” located at https://www.lighthouseoptics.com/product/autoclavable-video-adaptor/, visited on Apr. 8, 2022. (5 pages).

Lighthouse Optics. (Aug. 10, 2020) “Universal C-Mount Adaptor,” located at https://www.lighthouseoptics.com/product/universal-c-mount-adaptor/, visited on Apr. 8, 2022. (5 pages).

Lighthouse Optics. (Aug. 10, 2020) “V-mount Adaptor,” located at https://www.lighthouseoptics.com/product/v-mount-adaptor/, visited on Apr. 8, 2022. (5 pages).

* cited by examiner 204
306C
404
414
406
408B
604B
216
306B
504
418
612
218
306D
414
408A
604A
306A 204
306C
414
610B
408B
410
604B
606B
216
602B
306B
500B
600
418
504
218
404
500A
406
414
610A
306D
408A
604A
410
606A
602A
306A 1000
1008A
1006
1008B
218

218
1004
1006
1002
1000

ENDOSCOPIC CAMERA COUPLER

CROSS-REFERENCE TO RELATED APPLICATIONS

This application claims priority to and benefit of U.S. Provisional Patent Application No. 63/384,407, filed Nov. 18, 2022, the disclosure of which is hereby incorporated herein by reference in its entirety.

FIELD

The present invention pertains to the field of medical devices. More particularly, the present invention relates to endoscopic camera systems.

BACKGROUND

An endoscopic camera system includes an endoscope that is inserted into the body of a subject for delivering light to and receiving light from a surgical cavity. The endoscope is mounted to a camera head that can capture video and images based on the light received from the surgical cavity via the endoscope. The camera head can be communicatively coupled to a camera control unit that processes video and image data from the camera head for display or storage.

The camera head can include an optical coupler for releasable coupling of the endoscope to the camera head. The coupler can include optical components for focusing the light received from the endoscope onto the imaging sensor assembly in the camera head. To provide this focusing function, a coupler may include one or more optical components, such as one or more lenses or prisms, that can be moved relative to the camera, the endoscope, or both, to alter the focal distance.

An endoscope may be inserted into and removed from the coupler during an endoscopic procedure. For example, a surgeon may select a desired type and/or size of endoscope and may couple the endoscope to the camera head via the coupler. During the procedure, the surgeon may desire to switch to a different endoscope, such as to switch to an endoscope that provides a different field of view. Disconnecting and connecting of the endoscope from/to the coupler is generally performed when the endoscope is outside the body of the subject. To facilitate connection and disconnection of an endoscope from the coupler, couplers typically include release actuators that a user can actuate by hand to release the endoscope.

SUMMARY

According to an aspect, an endoscopic camera coupler includes a clamping assembly configured to engage an endoscope at multiple locations to clamp the endoscope more reliably to the coupler. The clamping assembly can include a clamp that is moved out of its clamping position by a user's press of a button. One or more clamping arms may be rotatably hinged, e.g. pinned, to the clamp at one end and may be configured to follow a predetermined path at the other end. Thereto, the arms can include a pin at the other end that rides in a slot. The orientation of the path, e.g. the slot, is such that movement of the rotatably hinged, e.g. pinned, end of the clamping arm, due to movement of the clamp to its unclamped position, causes the clamping arm to rotate outwardly, away from its clamping position. A spring may bias the button toward a non-depressed position such that when the user releases the button, the clamp and clamping arms move toward their clamping positions. An endoscope eyepiece inserted into the clamping assembly may be clamped at multiple spaced-apart locations by the clamp and one or more clamping arms, which can help ensure that the endoscope is properly positioned in the coupler.

According to an aspect, an endoscopic camera coupler includes a clamping assembly configured to engage an endoscope at multiple locations to clamp the endoscope more reliably to the coupler. The clamping assembly can include a clamp that is movable out of its clamping position by a user's press of a button. One or more clamping arms may be pivotally connected to the clamp, such that movement of the clamp out of its clamping position causes the one or more clamping arms to rotate away from their clamping positions.

According to an aspect, a coupler for coupling an endoscope to a camera head comprises a base configured to mount to the camera head and to receive an eyepiece of the endoscope; a clamp for clamping the eyepiece in the base, the clamp configured to move laterally relative to a longitudinal axis of the coupler between a clamping position and non-clamping position; at least one clamping arm pivotally connected to the clamp such that movement of the clamp from the non-clamping position to the clamping position causes the one or more clamping arms to rotate into engagement with the eyepiece; and a button for pressing by a user to move the clamp from the clamping position to the non-clamping position.

According to an aspect, a coupler for coupling an endoscope to a camera head includes a base configured to mount to the camera head and to receive an eyepiece of the endoscope; a clamp for clamping the eyepiece in the base, the clamp configured to move laterally relative to a longitudinal axis of the coupler between a clamping position and non-clamping position; at least one clamping arm rotatably connected to the clamp and configured to follow a predetermined path with respect to the base. The at least one clamping arm may be rotatably hinged, e.g. pinned, to the clamp at one end and may be configured to follow the predetermined path at the other end. Thereto, the at least one clamping arm can comprise a pin that moves in a slot of the base. When the clamp moves laterally toward the clamping position, the clamping arm following of the predetermined path, e.g. movement of the pin in the slot, causes the at least one clamping arm to rotate into engagement with the eyepiece. The clamp further includes a button for pressing by a user to move the clamp from the clamping position to the non-clamping position.

The clamp may be biased toward the clamping position. The clamp may extend from the button.

The button may be biased by at least one spring. The at least one spring may be located beneath the button.

The coupler may include a front cover attached to the base, and the clamp may be retained between the front cover and the base.

The clamp may be configured to engage the eyepiece at two or more spaced apart locations. The clamp may include at least two arms, and an end portion of each arm may be configured to engage the eyepiece at one of the two or more spaced apart locations. The clamp may include a semicircular portion that engages the eyepiece at the two or more spaced apart locations.

The at least one clamping arm may include first and second clamping arms.

The base may include a recess for receiving the eyepiece, and the clamp and the at least one clamping arm may be positioned outwardly of the recess when the clamp is in the non-clamping position.

The slot may be a straight slot.

The coupler may include a focus ring rotatably mounted to the base and configured to translate at least one optical component of the coupler to adjust a focus of the coupler, a plurality of seals that seal between the focus ring and a main body of the base, and at least one desiccant located within one or more pockets of the focus ring. The at least one desiccant may be retained within the one or more pockets by a band.

The focus ring may include a groove that receives a rib of the main body of the base forming a pathway to an associated seal of the plurality of seals that includes a plurality of ninety degree turns.

According to an aspect, a method of coupling an endoscope to a camera head includes pressing a button of a coupler mounted to the camera head, causing a clamp of the coupler to move laterally relative to a longitudinal axis of the coupler away from a clamping position; positioning an eyepiece of the endoscope at least partially in the coupler; and releasing the button, causing the clamp to move laterally to the clamping position and engage the eyepiece such that the eyepiece is retained in the coupler, wherein when the clamp moves laterally to the clamping position, at least one clamping arm rotates relative to the clamp into engagement with the eyepiece.

The clamp may be biased toward the clamping position. The at least one clamping arm may be rotatably connected to the clamp.

The at least one clamping arm, in particular an end of the clamping arm distant from the rotatable connection to the clamp, may be configured to follow a predetermined path relative to a base of the coupler when the at least one clamping arm rotates relative to the clamp. The at least one clamping arm may, e.g., include a pin that moves in a slot of the base of the coupler when the at least one clamping arm rotates relative to the clamp. Alternatively, or additionally, the at least one clamping arm may, e.g., include a slot that moves over a pin or ridge of the base of the coupler when the at least one clamping arm rotates relative to the clamp.

The predetermined path may be a straight path. The slot may be a straight slot. The ridge may be a straight ridge.

The clamp in the clamping position may engage the eyepiece at two or more spaced apart locations.

A first arm of the clamp may engage the eyepiece at a first one of the two or more spaced apart locations and a second arm of the clamp may engage the eyepiece at a second one of the two or more spaced apart locations.

The clamp may include a semicircular portion that engages the eyepiece at the two or more spaced apart locations.

According to an aspect, a camera head assembly includes a camera head; and a coupler comprising: a base mounted to the camera head and configured to receive an eyepiece of an endoscope, a clamp for clamping the eyepiece in the base, the clamp configured to move laterally relative to a longitudinal axis of the coupler between a clamping position and non-clamping position, at least one clamping arm rotatably connected to the clamp and configured to follow a predetermined path relative to the base. The at least one clamping arm may be rotatably hinged, e.g. pinned, to the clamp at one end and may be configured to follow the predetermined path at the other end. The at least one clamping arm can e.g. comprise a pin that moves in a slot of the base. When the clamp moves laterally toward the clamping position, the clamping arm following of the predetermined path, e.g. movement of the pin in the slot, causes the at least one clamping arm to rotate into engagement with the eyepiece. The clamp further includes a button for pressing by a user to move the clamp from the clamping position to the non-clamping position.

The clamp may be biased toward the clamping position. The clamp may extend from the button.

The button may be biased by at least one spring. The at least one spring may be located beneath the button.

The coupler may include a front cover attached to the base, and the clamp may be retained between the front cover and the base.

The clamp may be configured to engage the eyepiece at two or more spaced apart locations. The clamp may include at least two arms, and an end portion of each arm may be configured to engage the eyepiece at one of the two or more spaced apart locations. The clamp may include a semicircular portion that engages the eyepiece at the two or more spaced apart locations.

The at least one clamping arm may include first and second clamping arms.

The base may include a recess for receiving the eyepiece, and the clamp and the at least one clamping arm may be positioned outwardly of the recess when the clamp is in the non-clamping position.

The predetermined path may be a straight path. The slot may be a straight slot.

The coupler may include a focus ring rotatably mounted to the base and configured to translate at least one optical component of the coupler to adjust a focus of the coupler, a plurality of seals that seal between the focus ring and a main body of the base, and at least one desiccant located within one or more pockets of the focus ring. The at least one desiccant may be retained within the one or more pockets by a band.

The focus ring may include a groove that receives a rib of the main body of the base forming a pathway to an associated seal of the plurality of seals that includes a plurality of ninety degree turns.

It will be appreciated that any of the variations, aspects, features, and options described in view of the coupler apply equally to the clamp, camera head assembly and methods, and vice versa. It will also be clear that any one or more of the above variations, aspects, features, and options can be combined.

BRIEF DESCRIPTION OF THE FIGURES

The invention will now be described, by way of example only, with reference to the accompanying drawings, in which.

DETAILED DESCRIPTION

Figure 1:
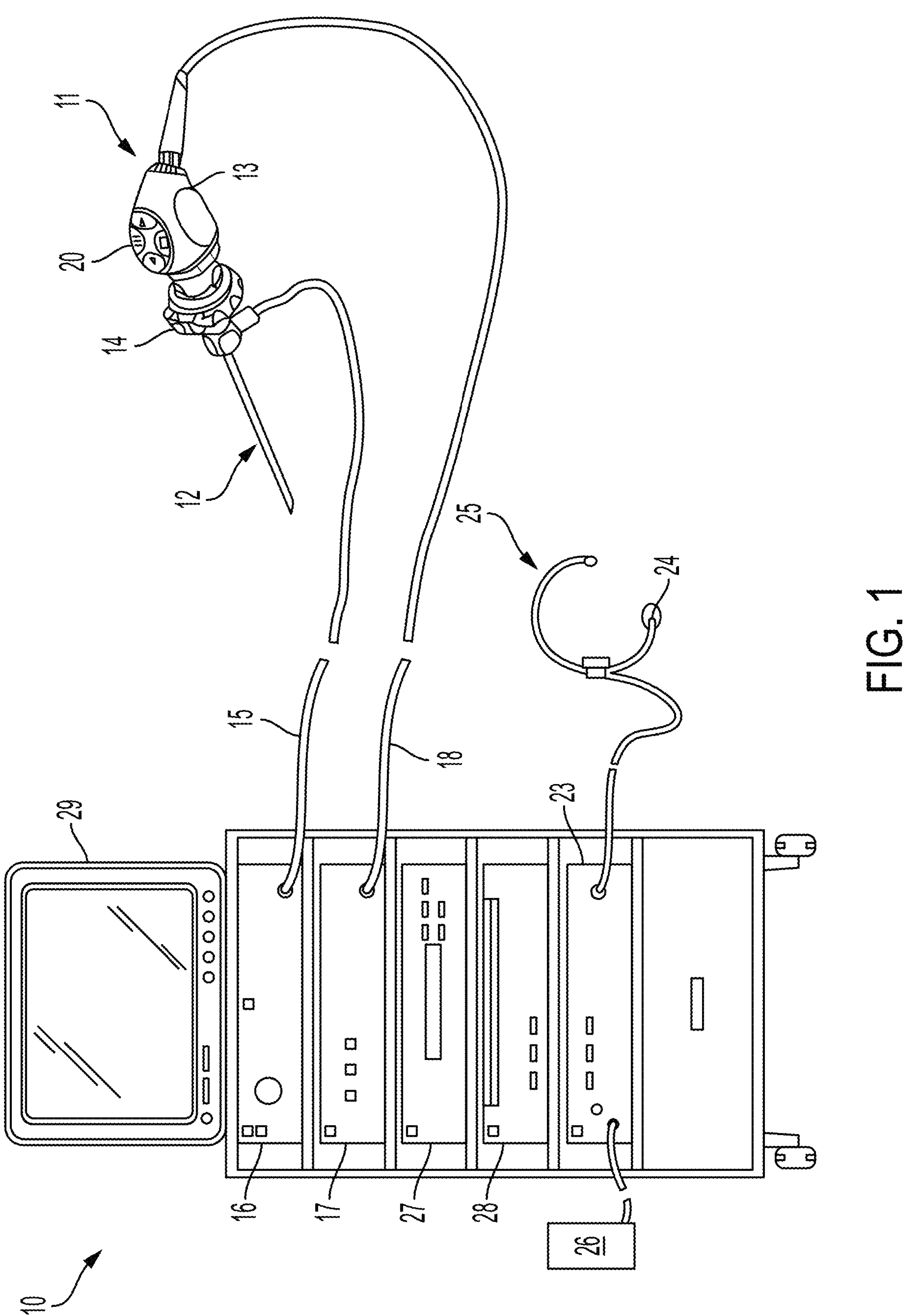
FIG. 1 illustrates an example of an endoscopic imaging system.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein is an endoscopic camera coupler that includes a clamping assembly configured to clamp an endoscope to the coupler such that the optical axes of the endoscope and coupler are substantially aligned. The clamping assembly engages the eyepiece of an endoscope inserted in the clamping assembly at multiple spaced-apart locations that can be distributed about a circumference of the eyepiece. This distribution of engagement locations can help center the eyepiece with respect to the coupler and can help prevent cocking of the endoscope.

The clamping assembly can be actuated by a button that may be easily accessible to a user. For example, a user can depress the button to actuate the clamping assembly into its unclamped position. The user may be able to depress the button with a finger (e.g., thumb) of the same hand that is holding the camera head, freeing the user's other hand to handle the endoscope.

The button may be coupled to a clamp such that depressing the button causes the clamp to move laterally relative to an optical axis of the coupler to its unclamped position in which the clamp is positioned outwardly of a receptacle for the endoscope eyepiece. One or more clamping arms may be rotatably connected to the clamp. The one or more clamping arms may be configured to follow a predetermined path. The predetermined path may be configured such that movement of the clamp causes the one or more clamping arms to rotate outwardly to unclamped positions in which the one or more clamping arms are located outwardly of the receptacle. The one or more clamping arm may be rotatably hinged, e.g. pinned, to the clamp at one end and may be configured to follow the predetermined path at the other end. The one or more clamping arms may include pins that ride in respective slots that are configured such that movement of the clamp causes the one or more clamping arms to rotate outwardly to unclamped positions in which the one or more clamping arms are located outwardly of the receptacle.

The button may be biased toward a non-depressed position such that a user release of the button causes the button to return to its non-depressed position. This moves the clamp toward its clamping position in which one or more clamping features of the clamp engage the eyepiece. The one or more arms rotate back toward their clamping positions in which they engage the eyepiece. The clamping features of the clamp and the one or more clamping arms can be positioned about the circumference of the eyepiece such that the eyepiece is engaged at locations that are substantially evenly distributed about the eyepiece. This even distribution of clamping force can help center the eyepiece in the coupler and can help ensure that the endoscope is not clamping in a cocked position.

The coupler can include various features for preventing fogging of optical components of the coupler. The clamping assembly can include relatively large vents that allow for ambient air to circulate into the space between the eyepiece and the optical components of the coupler, which can help reduce the trapping of moisture that could condense onto the eyepiece of coupler optical components. The coupler can include a focus ring that engages with a main body of the coupler with interlocking ribs and grooves that create a serpentine path that terminates at a seal. This serpentine path and seal help prevent water from penetrating into the interior of the coupler. Should any moisture make it past the seal, the coupler can include desiccant positioned in pockets in the focus ring and held in place by a band.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain terminology is used in this description for convenience and reference only and is not limiting. For example, the words "upwardly," "downwardly," "rightwardly," and "leftwardly" refer to directions in the drawings to which reference is made. The words "inwardly" and "outwardly" refer to directions toward and away from, respectively, the geometric center of the arrangement and designated parts thereof. The words "forwardly" and "distally" refer to the direction toward the end of the arrangement that is closest to the subject, and the words "rearwardly" and "proximally" refer to the direction toward the end of the arrangement which is furthest from the subject. This terminology includes the words specifically mentioned, derivatives thereof, and words of a similar nature.

FIG. 1 illustrates an example of an endoscopic imaging system 10. Endoscopic imaging system 10 includes an endoscope assembly 11 that can be used for visualizing inside of a subject's body during an endoscopic procedure. The endoscope assembly 11 includes an endoscope 12 coupled to a camera head 13 by a coupler 14 that forms the distal portion of the camera head 13. Light is provided to the endoscope 12 by a light source 16 via a light cable 15, which can be, for example, a fiber optic cable. The endoscope 12 directs the light from the light cable 15 to the area of interest within the subject's body, receives light reflected from the area of interest, and conveys light to an imager within the camera head 13. The imager is comprised of one or more image sensors that convert the optical image into electrical signals.

The camera head 13 may be connected to a camera control unit (CCU) 17 by a camera cable 18. The camera cable 18 can convey imaging data from the camera head 13 to the CCU 17 for display on display 29. In some embodiments, various control signals are transmitted bi-directionally between the camera head 13 and the CCU 17 via the camera cable 18.

A user interface 20 can be provided on the camera head 13 for enabling a user to manually control various functions of the endoscopic imaging system 10. According to some embodiments, various functions of the endoscopic imaging system 10 may be controlled by voice commands received by a microphone 24 mounted on a headset 25 worn by the surgeon and coupled to the voice-control unit 23, which can be coupled to the CCU 17. A hand-held control device 26, such as a tablet with a touch screen user interface, may be coupled to the voice-control unit 23 as a further control interface. In some embodiments, an imaging system controller 27 can be included and connected to one or more system components, such as the CCU 17 and/or the light source 16. According to various embodiments, the imaging system controller 27 provides further processing of image data from the CCU 17, controls display and storage of image data and communication of imaging or other data to a hospital network, and/or communicates control commands to connected system components. In some embodiments, a printer 28 may be included for printing hard copies of one or more images.

Figure 2:
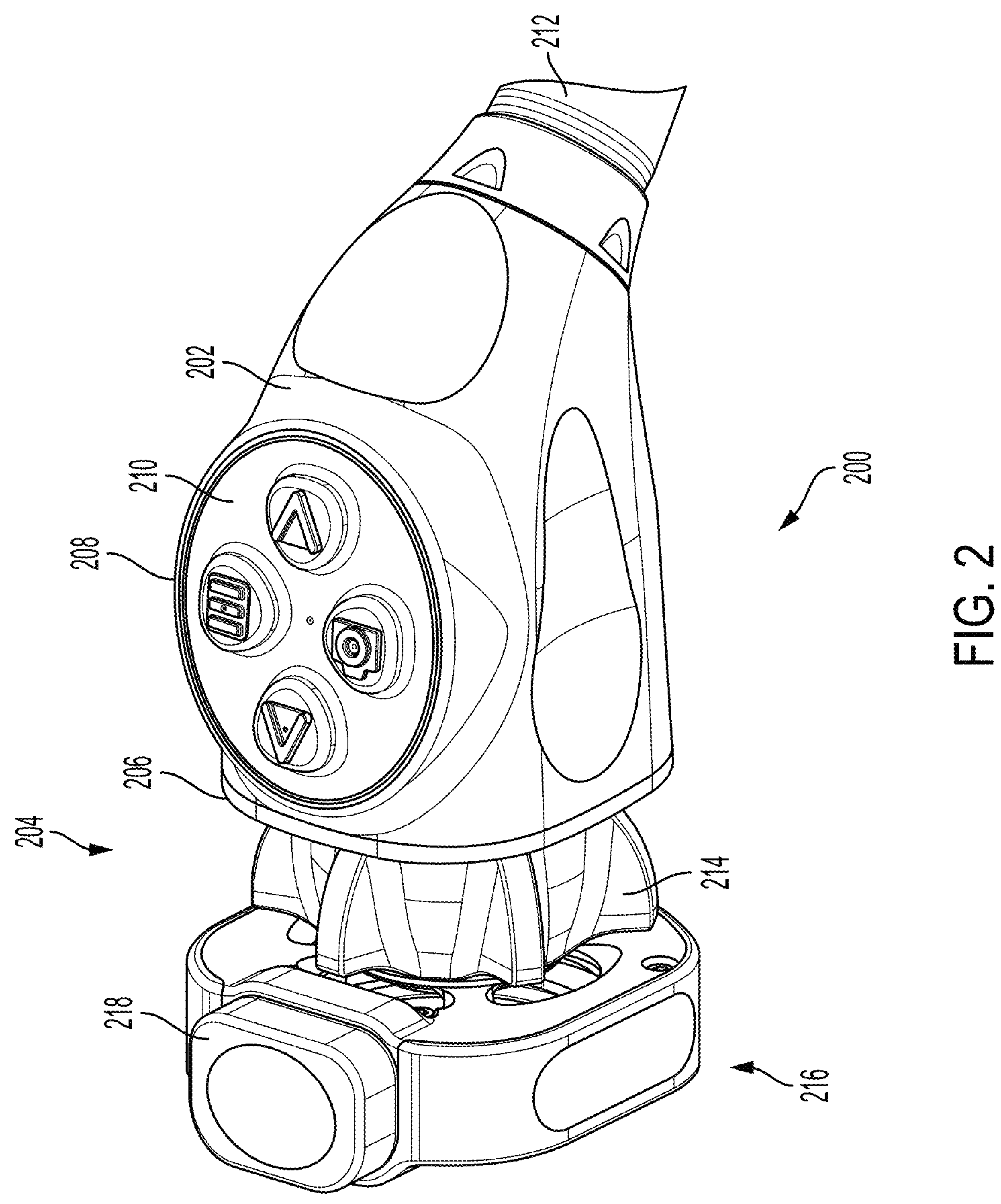
FIG. 2 is a perspective view of an exemplary camera head that can be used for the endoscopic imaging system of FIG. 1.

FIG. 2 is a perspective view of an exemplary camera head 200 that can be used for endoscopic imaging system 10, according to various embodiments. The camera head 200 includes a main enclosure 202 and a coupler 204 that extends forwardly from the main enclosure 202. The main enclosure 202 can include two main enclosure parts-a front enclosure part 206 and a rear enclosure part 208. A user interface 210 can be sealably attached to the rear enclosure part 208. A camera cable 212 may extend from the rear enclosure part 208. The coupler 204 extends forwardly from the front enclosure part 206 and can be removably mounted to the front enclosure part 206, such as via a threaded engagement.

The coupler 204 can include one or more focusing optical components (described further below) and a focus ring 214 that, when rotated, adjusts a position of one or more optical components to adjust a focus provided by the coupler 204. The coupler 204 includes a clamping assembly 216 for releasably clamping an endoscope to the camera head 200. The clamping assembly 216 includes a button 218 that is biased toward clamping and that the user presses to unclamp an endoscope positioned in the clamping assembly 216. The clamping assembly 216 can be configured so that a user can clamp and unclamp an endoscope with one hand.

Figures 3A, 3B:
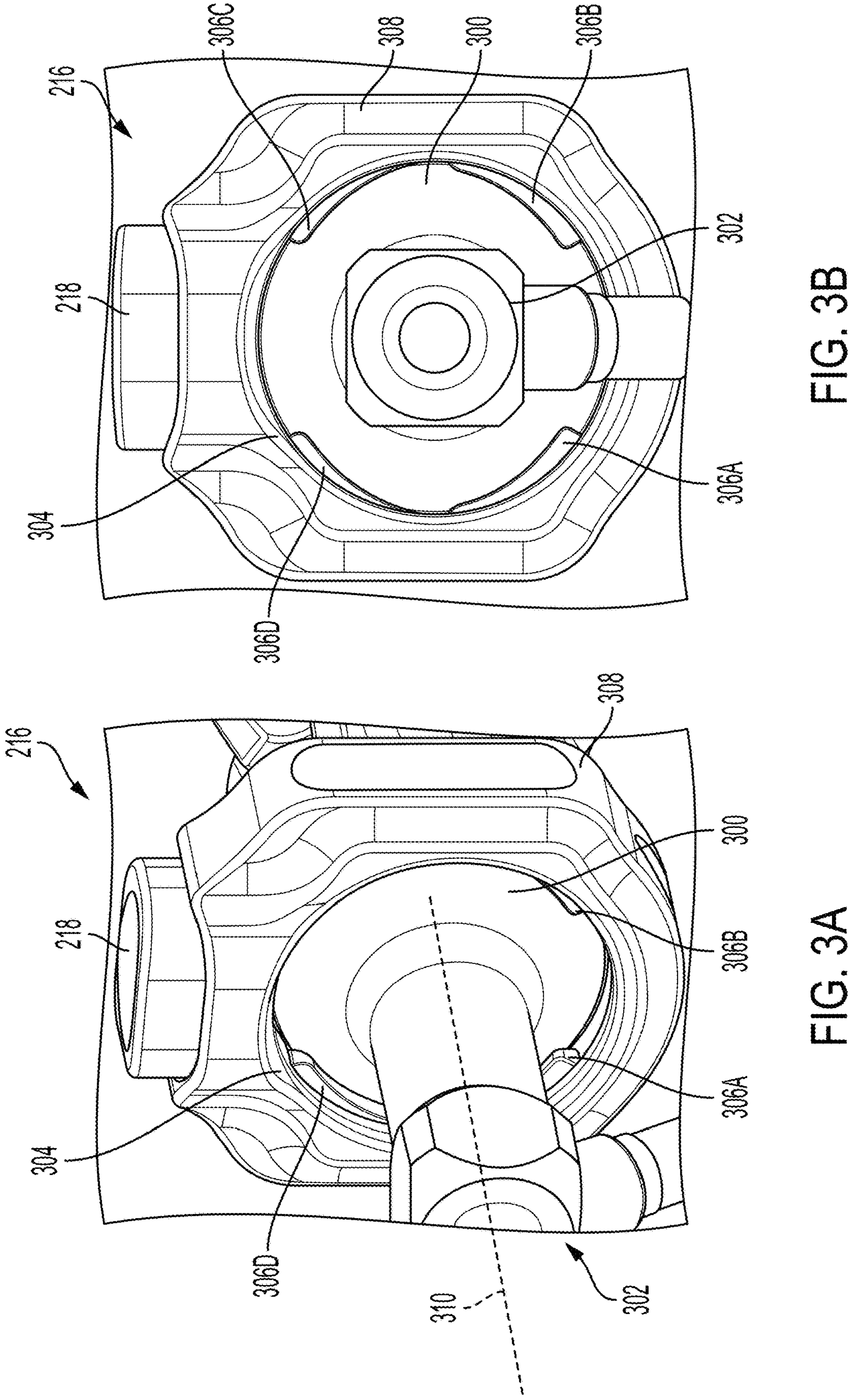
FIG. 3A and FIG. 3B are perspective and front views, respectively, of an exemplary clamping assembly.

FIGS. 3A and 3B are perspective and front views, respectively, of the clamping assembly 216 clamping the eyepiece 300 of an exemplary endoscope 302. The clamping assembly 216 includes a front cover 308 that can include an opening 304 that permits the eyepiece 300 to be moved into and out of the clamping assembly 216. The clamping assembly 216 includes a plurality of clamping features 306A, 306B, 306C, and 306D that can move laterally relative to an optical axis 310 of the endoscope 302 into and out of engagement with the eyepiece 300 to clamp the eyepiece 300 in the clamping assembly 216. The clamping features 306A-D are shown in their clamping positions in the example of FIGS. 3A and 3B, which correspond to the button 218 being in its non-depressed position as shown in FIGS. 3A and 3B. The clamping features 306A-D can engage the eyepiece 300 at multiple spaced-apart locations that are distributed about the circumference of the eyepiece 300, which can better center the endoscope 302 with respect to the coupler 204 such that the optical axis 310 of the endoscope 302 is substantially aligned with the optical axis of the coupler 204. Better alignment of the optical axis 310 of the endoscope 302 with that of the coupler 204 can result in better image quality.

As described further below, depressing the button 218 causes the clamping features 306A-D to move laterally out of engagement with the eyepiece 300 and outwardly from the opening 304 of the front cover 308 so that the endoscope 302 can be removed from the clamping assembly 216. The button 218 may be configured such that a user can depress the button 218 with a finger (e.g., thumb) of the same hand that is holding the camera head.

Figure 4:
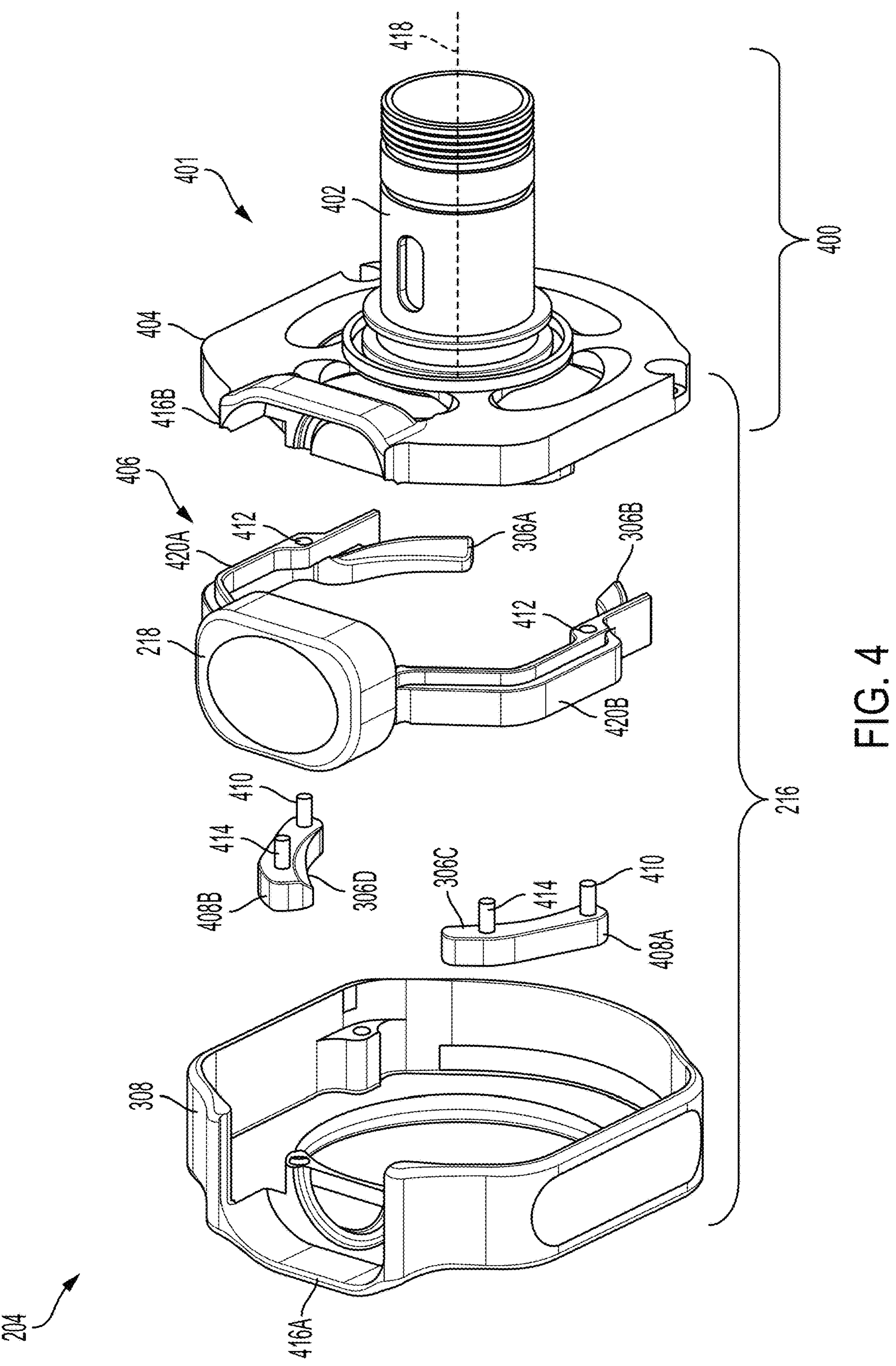
FIG. 4 is an exploded view of an exemplary coupler.

FIG. 4 is an exploded view of various aspects of the coupler 204. The coupler 204 includes a base 400 that can include a main body 401. The main body 401 can include an optics housing 402 for housing one or more optical components aligned along an optical axis 418. The main body 401 can provide a rear housing piece 404 of the clamping assembly 216. The front cover 308 can be assembled to the rear housing piece 404. Together, the rear housing piece 404 and front cover 308 can house a clamp 406 and one or more clamping arms 408A and 408B. Each of the front cover 308 and the rear housing piece 404 can include respective button housing portions 416A and 416B, respectively, that together form a housing for the button 218.

The clamp 406 can include the clamping features 306A,B, which, as discussed above, engage with the eyepiece of the endoscope. The clamp 406 may be integrally formed with button 218, as shown, or the clamp 406 and button 218 can be separate components that are assembled together. The clamp 406 may include two arms 420A,B, with each clamping feature 306A,B being located at end portions of the arms 420A,B.

The clamping arms 408A,B can include the clamping features 306C, D, respectively. Although two clamping arms are shown, it should be understood that fewer or a greater number of clamping arms may be included. The clamping arms 408A,B each can include pins 410 that assemble into associated holes 412 of the clamp 406 such that the clamping arms 408A,B are pivotably connected to the clamp 406. The pins 410 may be integral with the clamping arms 408A,B. Alternatively, the pins 410 may be integral with the clamp 406. The clamping arms 408A,B can also be pivotably connected to the clamp 406 in other manners, such as by living hinges, snap connections or the like. The clamping arms 408A,B can also include pins 414 that assemble into associated slots (not shown in figure) of the rear housing piece 404, as discussed further below. The pins 414 may be integral with the clamping arms 408A,B.

Figure 5:
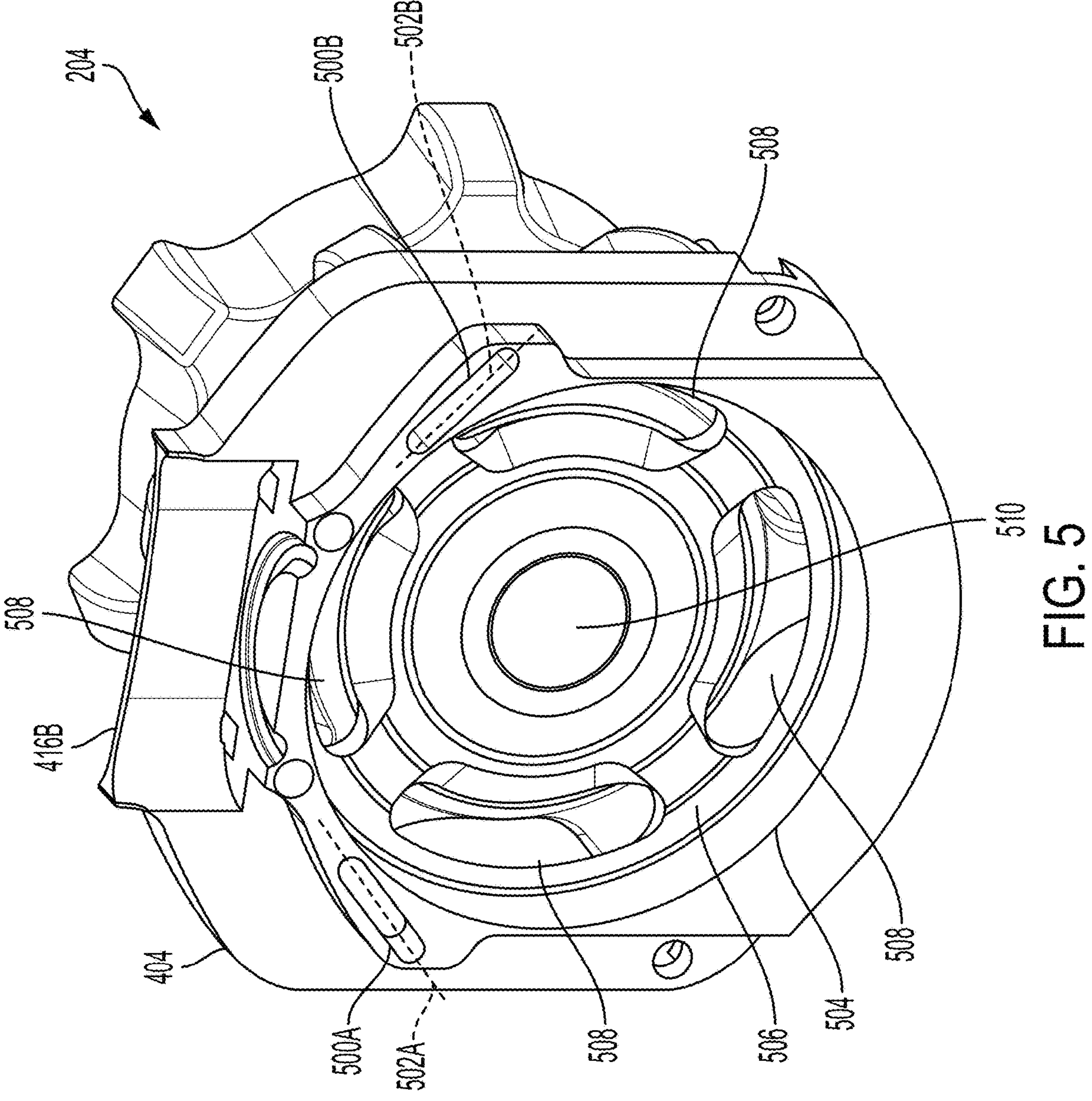
FIG. 5 is a front perspective view of a rear housing piece of the coupler of FIG. 4 illustrating an example of slots that receive the pins of clamping arms.

FIG. 5 is a front perspective view of the rear housing piece 404 illustrating an example of slots 500A,B that receive the pins 414 of the clamping arms 408A,B shown in FIG. 4. The slots 500A,B can extend in a straight line as indicated by straight axes 502A,B or can be curved.

The rear housing piece 404 can include a recess 504 for seating the eyepiece of the endoscope (e.g., eyepiece 300 of endoscope 302 shown in FIGS. 3A and 3B). The diameter of the recess 504 is larger than an outer diameter of the eyepiece of an endoscope or range of endoscopes for which the coupler is designed. The recess 504 can include a shoulder 506 against which the proximal end of the eyepiece rests.

The rear housing piece 404 can include one or more vents 508 to ventilate the space behind the eyepiece of the endoscope, which can be useful for preventing fogging of an optical component at the proximal end of the eyepiece and/or a window 510 of the coupler 204.

Figures 6A, 6B:
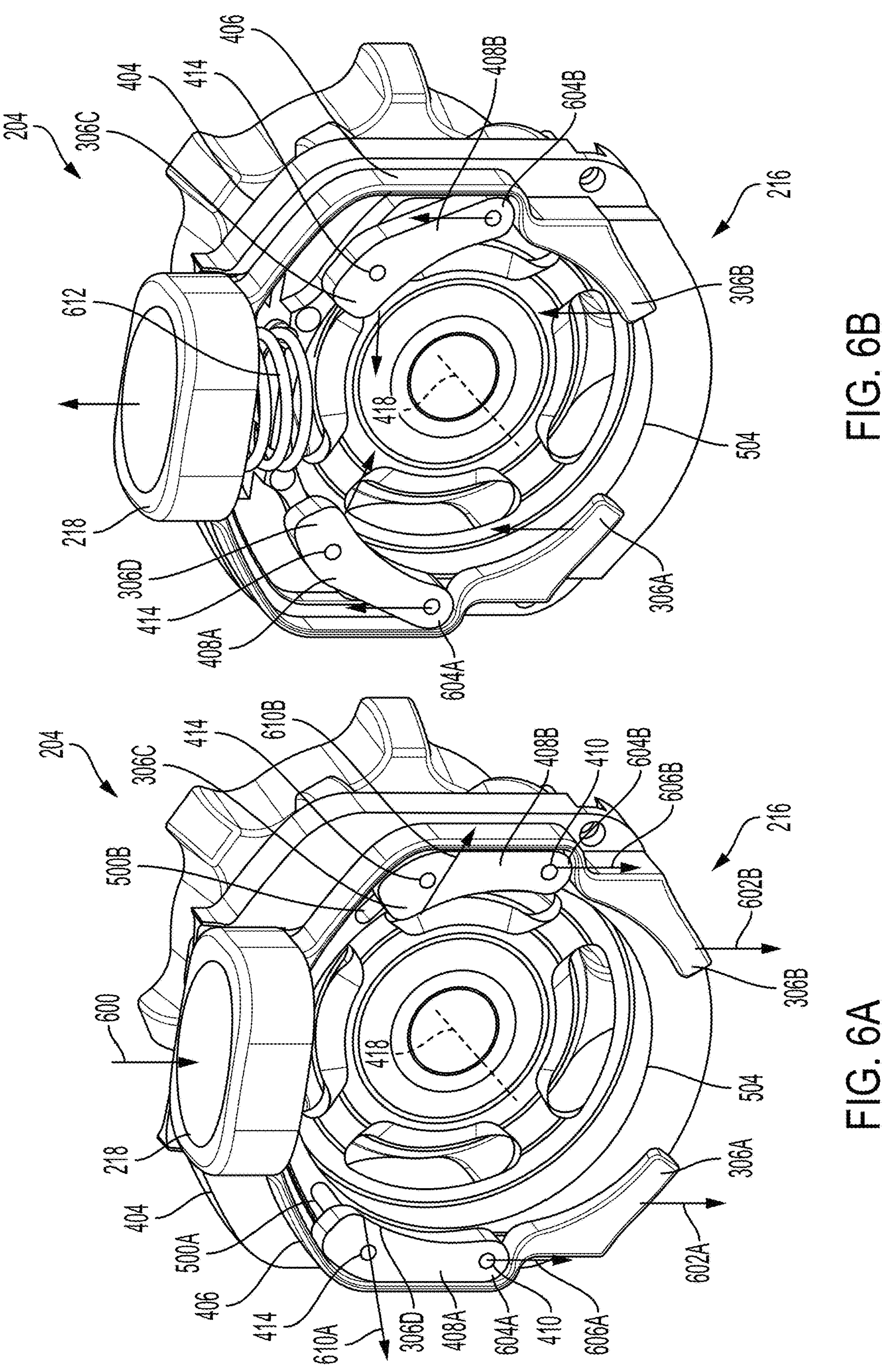
FIG. 6A and FIG. 6B are front perspective views of the coupler of FIG. 4 without the front cover.

FIGS. 6A and 6B are front perspective views of the coupler 204 without the front cover 308 (sec FIGS. 3A and 3B). FIG. 6A shows the clamping assembly 216 in a non-clamping configuration and FIG. 6B shows the clamping assembly 216 in a clamping configuration. In FIG. 6A, the button 218 has been depressed, such as by a user, as indicated by arrow 600. Since the button 218 and the clamp 406 are coupled (e.g., integrally formed or assembled), the clamp 406 moves laterally relative to the optical axis 418 in a downward direction with respect to the view shown in FIG. 6A as indicated by arrows 602A,B. This moves the clamping features 306A,B laterally relative to the optical axis 418 to a position that is outward of the recess 504. Since each clamping arm 408A,B hingedly connected to the clamp 406, the hingedly connected ends 604A,B move downward with the clamp 406 as indicated by arrows 606A,B. Here, since each clamping arm 408A,B is pinned via pin 410 to the clamp 406, the pinned ends 604A,B move downward with the clamp 406 as indicated by arrows 606A,B. The opposite ends of the clamping arms 408A,B and the base 400, e.g. the rear housing piece 404, are configured such that the opposite ends follow a predetermined path with respect to the rear housing piece 404 when the clamp 406 moves laterally relative to the optical axis 418. Here, the pins 414 ride within slots 500A,B, causing the clamping arms 408A,B to pivot outwardly about pin 410. Alternatively, the clamping arms 408A,B can each comprise a slot, and pins can be fixed relative to the base 400, e.g. to the rear housing piece 404, such that the slots ride about the pins causing the clamping arms 408A,B to pivot outwardly about pins. The pins may be integral with the rear housing piece 404. The downward and outward movement of the clamping arms 408A,B causes the clamping features 306C, D to move downward and outward as indicated by arrows 610A,B to such an extent that when the button 218 is fully depressed, the clamping features 306C, D are outward of the recess 504. With the clamping assembly 216 in this non-clamping configuration, a user can insert an eyepiece of an endoscope into the recess 504 and/or remove the endoscope from the recess 504.

FIG. 6B shows the clamping assembly 216 in the clamping configuration. In this configuration, the button 218 is in a non-depressed position. The button 218 may be biased toward this position by a spring 612, which can be a coil spring as shown, a wave spring, or any other suitable biasing component. The spring 612 may be located within the button housing (see 416A,B of FIG. 4) beneath the button 218. The spring 612 may be sized to be pressable by a user's thumb, or other finger, and to create engagement forces between the clamping features 306A-D and the endoscope to center the endoscope within the recess 504.

Movement of the button 218 upward to the non-depressed position causes the clamp 406 to move upward to a clamping position in which the clamping features 306A,B are located inward of the outer diameter of the recess 504. The hinged, here pinned, ends 604A,B of the clamping arms 408A,B move upward with the clamp 406. Due to the sliding engagement between the pins 414 and the slots 500A,B, clamping arms 408A,B rotate inward to clamping positions in which the clamping features 306C, D are located within the outer diameter of the recess 504.

Figure 7:
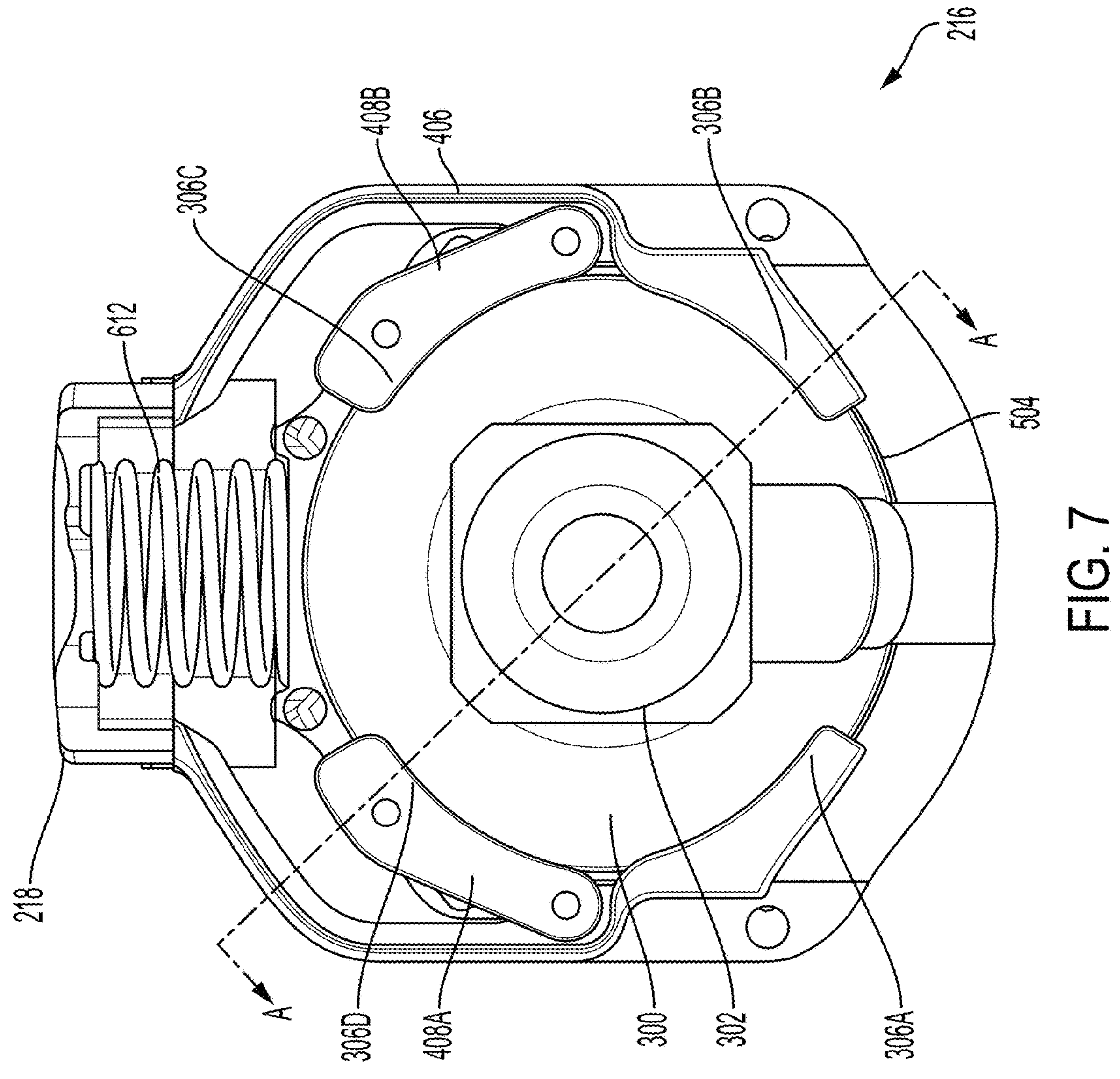
FIG. 7 is a front view of a clamping assembly in its clamping configuration.

FIG. 7 is a front view of the clamping assembly 216 in its clamping configuration with the front cover 308 (see FIGS. 3A and 3B) hidden to illustrate engagement between the clamping feature 306A-D and the eyepiece 300 of the endoscope 302. The eyepiece 300 is seated within the recess 504. The button 218 is in its non-depressed position. The clamp 406 is in its clamping position in which the clamping features 306A,B are pressed against the eyepiece 300 due to the biasing force of the spring 612. The clamping arms 408A,B are pivoted inwardly to their clamping positions in which the clamping features 306C, D are pressed against the eyepiece 300 due to the biasing force of the spring 612. Thus, the eyepiece 300 is held in place at four spaced-apart locations by the four clamping features 306A-D. The four locations are distributed about the circumference of the eyepiece 300, which distributes the clamping force around the circumference of the eyepiece 300. The clamping of the eyepiece 300 in multiple spaced-apart locations around the circumference of the eyepiece 300 can help ensure that the endoscope 302 is not cocked within the recess 504. This clamping arrangement can also help ensure that the endoscope 302 is centered within the recess 504 such that an optical axis of the endoscope 302 is substantially aligned with an optical axis of the coupler 204 as described above with respect to FIGS. 3A and 3B.

Figure 8:
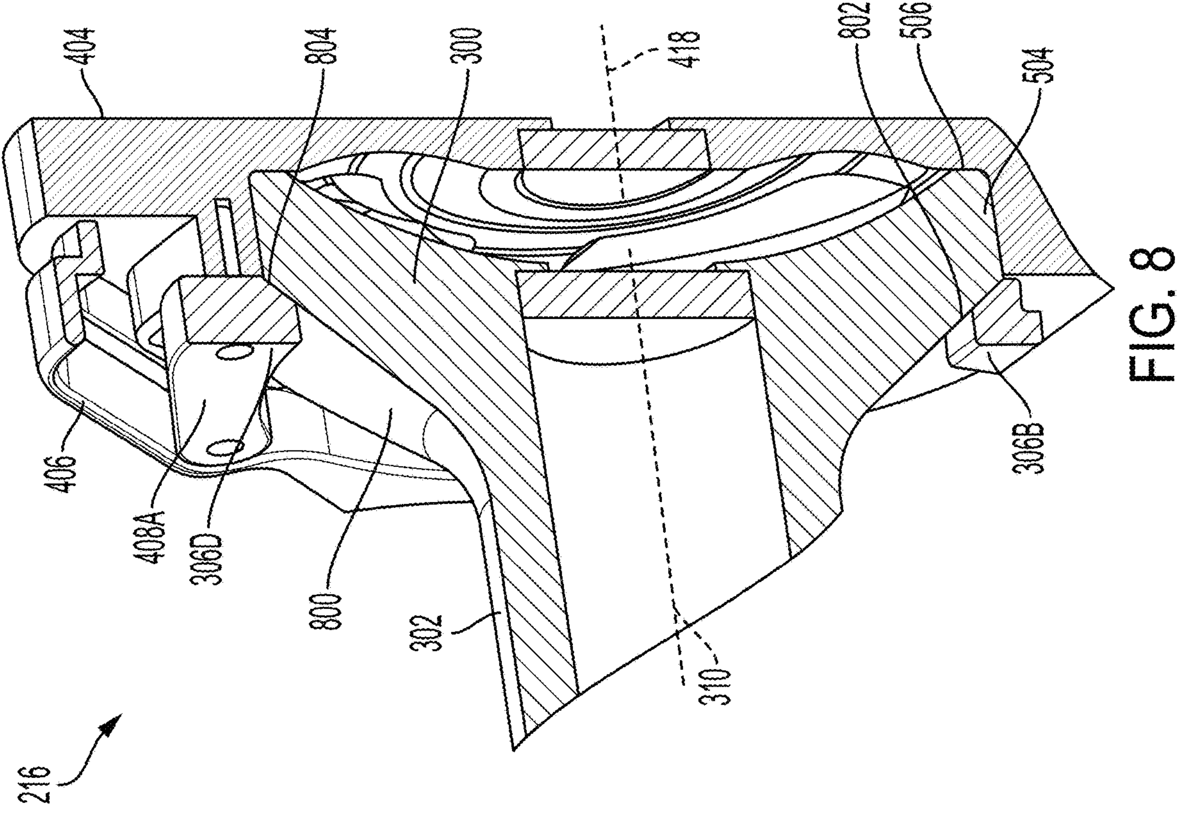
FIG. 8 is a cross section through line A-A of FIG. 7.

FIG. 8 is a cross section of a portion of the clamping assembly 216 through line A-A of FIG. 7. The clamping assembly 216 is in its clamping configuration. The eyepiece 300 of the endoscope 302 is seated in the recess 504 against the shoulder 506 of the rear housing piece 404. The clamping feature 306B of the clamp 406 is pressed against the tapered outer surface 800 of the eyepiece 300. The clamping arm 408A is in its clamping position such that its clamping feature 306D is pressed against the tapered outer surface 800 of the eyepiece 300 at a location that is opposite the interface of the clamping feature 306B and the eyepiece 300. The clamping feature 306B of the clamp 406 can include a tapered surface 802 configured to provide a surface contact with the tapered outer surface 800 of the eyepiece 300. Similarly, the clamping feature 306D can include a tapered surface 804 configured to provide a surface contact with the tapered outer surface 800 of the eyepiece 300. The clamp 406 and clamping arms 408A,B force the eyepiece 300 against the shoulder 506 of the recess 504 and can help center the eyepiece 300 within the recess 504 such that the optical axis 310 of the endoscope 302 substantially aligns with the optical axis 418 of the coupler 204.

Figure 9:
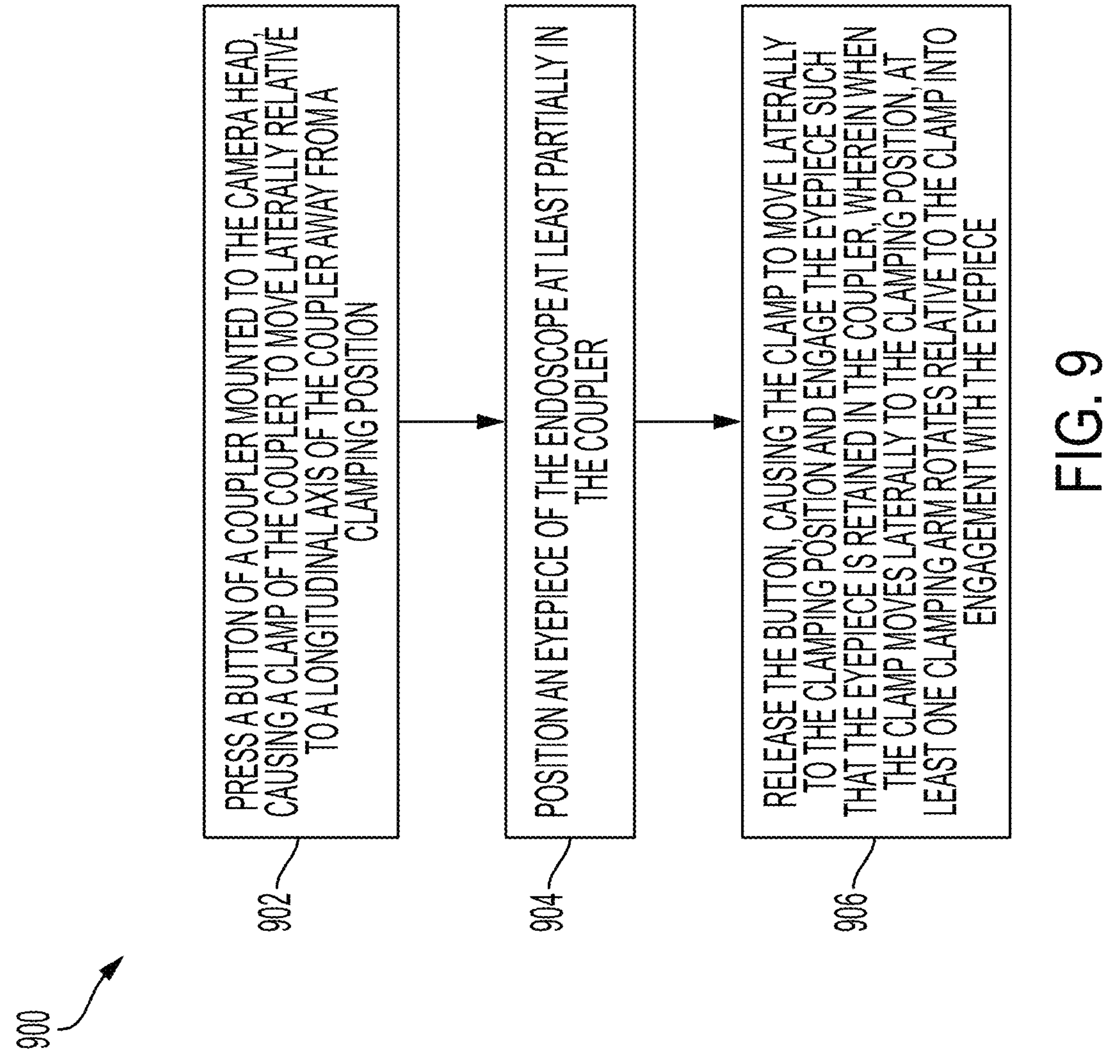
FIG. 9 is a flow diagram of a method of coupling an endoscope to a camera head.

FIG. 9 is a flow diagram of a method 900 of coupling an endoscope, such as endoscope 12 of FIG. 1, to a camera head, such as camera head 200 of FIG. 2. It will be appreciated that this method is only concerned with the coupling of the endoscope to the camera head without any functional link between the method and effects produced by the endoscope on the body. At step 902, a button of a coupler mounted to the camera head is pressed, causing a clamp of the coupler to move laterally relative to a longitudinal axis of the coupler away from a clamping position. For example, with respect to FIG. 6A, the button 218 may be pressed by a user in a downward direction relative to the view of FIG. 6A causing the clamp 406 to move downward away from its clamping position, which is shown in FIG. 6B. The button can be pressed by a user holding the camera head. The user may hold the camera head with one hand and may press the button with a finger (e.g., a thumb) of that hand.

The movement of the clamp may cause one or more clamping arms pivotably connected to the clamp to rotate away from their clamping positions. For example, clamping arms 408A,B of FIG. 6A may rotate away from their clamping positions (shown in FIG. 6B) as indicated by arrows 610A,B due to their pivot engagement with the clamp 406 and the engagement of their pins 414 in the slots 500A,B of the rear housing piece 404.

At step 904, an eyepiece of the endoscope is positioned in the coupler. For example, with respect to FIG. 6A, with the clamp 406 and the clamping arms 408A,B in their unclamped positions and out of the way of the recess 504, an eyepiece of the endoscope can be positioned in the recess 504. The user may continue to press the button while positioning the eyepiece in the coupler. The user may hold the camera head with one hand, continue to press the button with a finger of that same hand, and may use the other hand to hold the endoscope and position its eyepiece in the coupler.

At step 906, the button may be released, causing the clamp to move laterally to the clamping position and engage the eyepiece such that the eyepiece is retained in the coupler. The movement of the clamp to its clamping position may cause at least one clamping arm to rotate relative to the clamp into engagement with the eyepiece. For example, with respect to FIG. 8, the clamp 406 is in its clamping position such that its clamping feature 306B is in engagement with the eyepiece 300. The clamping arm 408A has moved into its clamping position such that it is in engagement with the eyepiece 300.

Figures 10A, 10B:
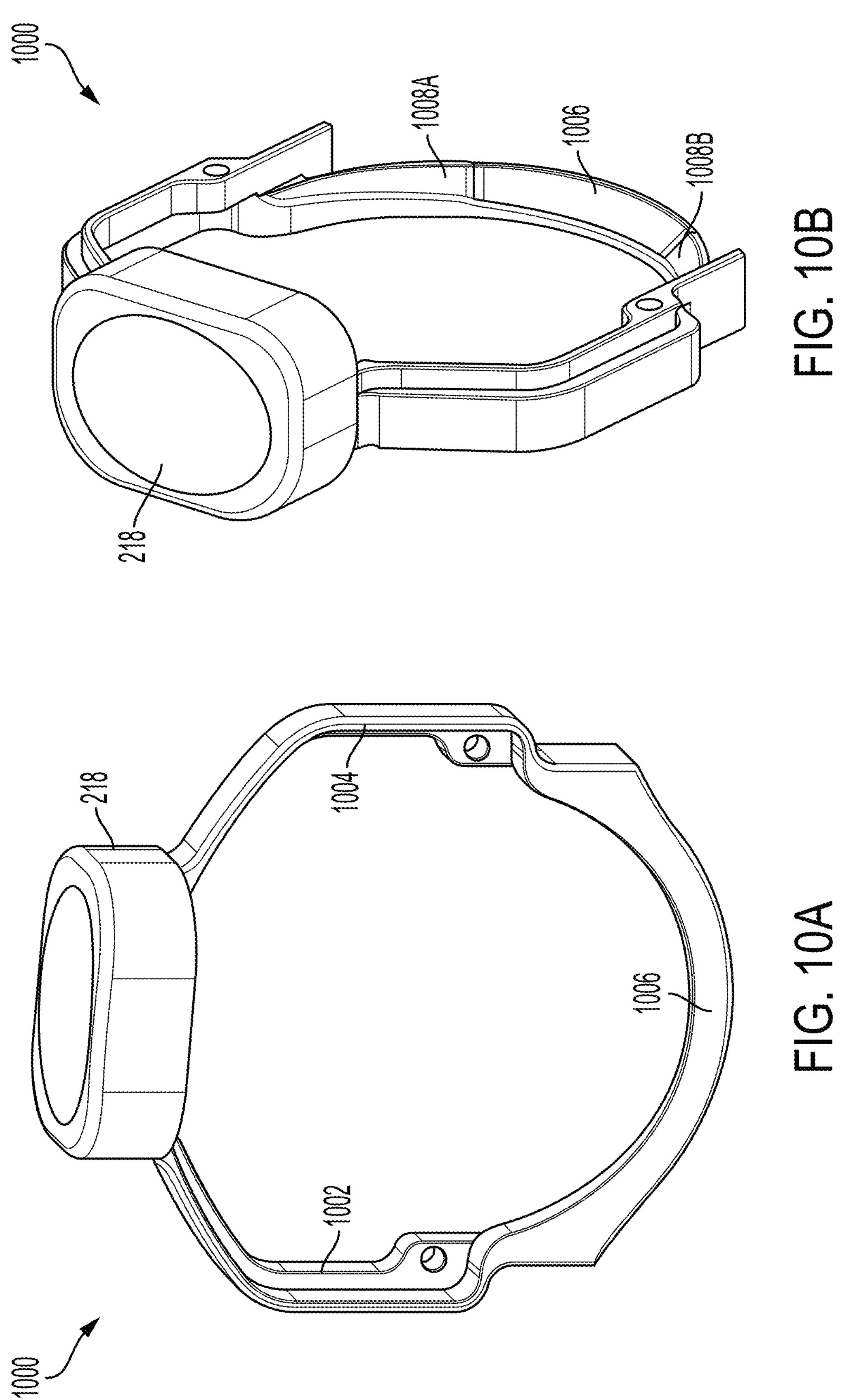
FIG. 10A and FIG. 10B illustrate an exemplary clamp.

FIGS. 10A and 10B illustrate a clamp 1000 that can be used in place of clamp 406 shown in FIG. 4. Relative to clamp 406, the two arms 1002 and 1004 of clamp 1000 are connected by a center section 1006 forming a semi-circular portion 1008 opposite the button 218. The center section 1006 can be continuous with the clamping features 1008A,B forming a continuous semi-circular clamping surface that can engage a corresponding continuous semi-circular portion of the eyepiece. Alternatively, the center section 1006 can be configured to not engage with the eyepiece.

Figure 11:
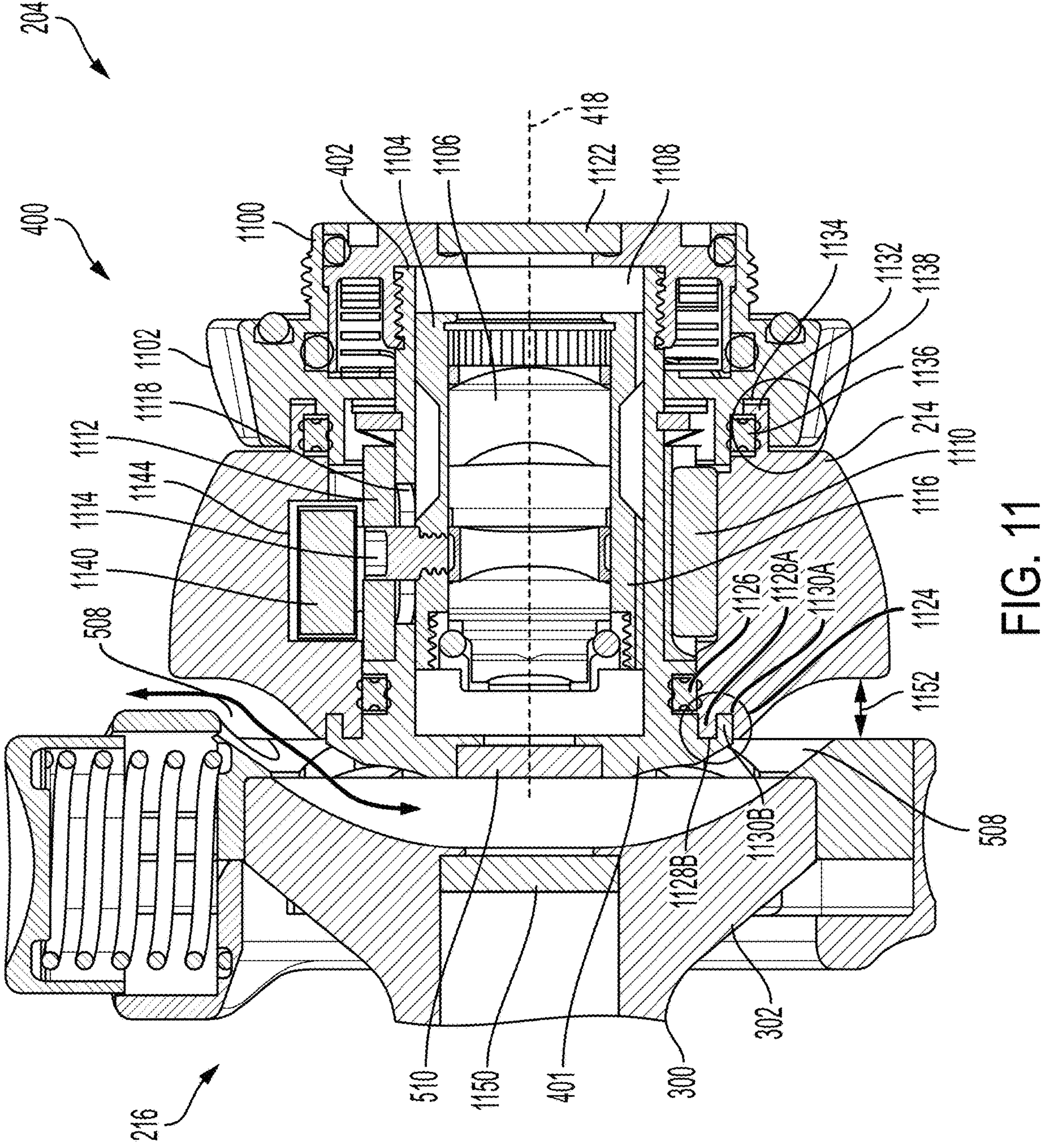
FIG. 11 is a cross-section of an exemplary coupler.

FIG. 11 is a cross-section of coupler 204 with an endoscope 302 clamped in the clamping assembly 216. The base 400 of the coupler 204 can include a threaded coupling piece 1100 for threading to the main enclosure 202 of a camera head 200 (see FIG. 2). A user may grasp a ring 1102 of the coupling piece 1100 for threading the coupling piece 1100 onto the main enclosure 202. Located within the optics housing 402 can be an optics assembly 1104 that can include one or more optical components, such as one or more lenses 1106. The optics assembly 1104 may move in the direction of the optical axis 418 to change the focus provided by the coupler 204. The focus may be adjusted by user rotation of the focus ring 214. The focus ring 214 may be coupled (via pin 1110) to a ring 1112 such that the ring 1112 rotates with the focus ring 214. The ring 1112 has a helical groove (not shown). A pin 1114 rides within the helical groove. The pin 1114 is fixedly connected to a housing 1116 of the optics assembly 1104 and extends through a slot 1118 of the optics housing 402, which prevents the pin 1114 from rotating about the optical axis 418. Rotation of the focus ring 214 rotates the ring 1112. Due to the engagement of the pin 1114 with the helical groove of the ring 1112, rotation of the helical groove causes the pin 1114 to translate, which translates the optics assembly 1104 along the optical axis 418.

The chamber 1108 of the optics housing 402 within which the optics assembly 1104 is located may be sealed by a window 510 located at a distal end of the optics housing 402 and a proximal window 1122 located at a proximal end of the optics housing 402. Moisture present in the chamber 1108 could lead to fogging of the one or more of the optical components of the optics assembly 1104, the window 510, and/or the proximal window 1122. To prevent fogging, the coupler 204 can include a number of features that prevent moisture from accessing this area (such as during use and/or during a cleaning procedure). One such feature is the configuration of the distal engagement 1124 between the focus ring 214 and the main body 401. The focus ring 214 and the main body 401 are designed such that their engagement at this location creates a serpentine path to a seal 1126. This serpentine path, which includes a number of ninety degree turns, causes a drop in pressure of any liquid stream entering that location (such as during a sterilization process) such that the pressure of the liquid at the seal 1126 is relatively low. The serpentine path is created by corresponding ribs 1128A, 1128B and grooves 1130A, 1130B formed in the focus ring 214 and main body 401.

A similar serpentine path is located at a proximal portion of the focus ring 214 where the focus ring 214 engages with the coupling piece 1100, as indicated by reference numeral 1138. The focus ring 214 includes a rib 1132 that fits into a groove 1134 of the coupling piece 1100, creating a pathway to a seal 1136 that includes a number of ninety degree turns. The seals 1126 and 1136 may be, for example, a quad-ring (as shown), an O-ring, or any other suitable seal.

Figure 12:
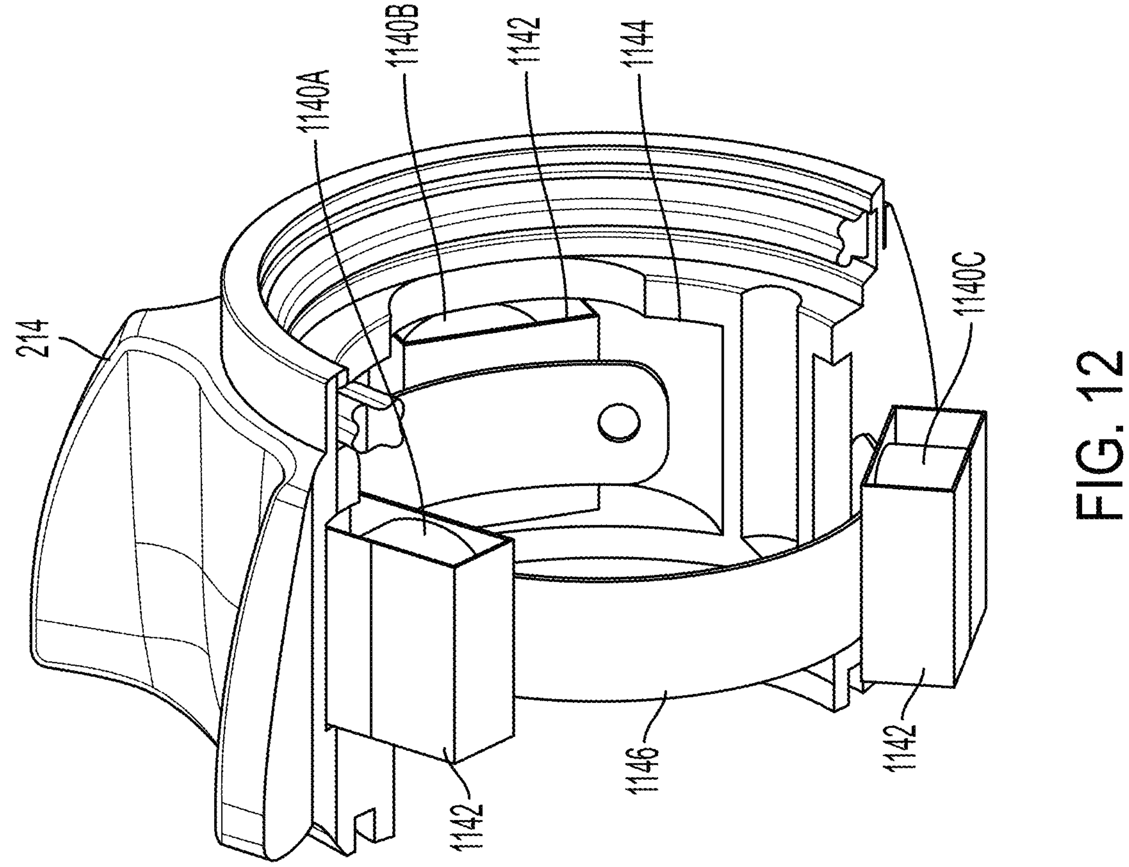
FIG. 12 illustrates a partial cutaway view of the focus ring with a number of pieces of desiccant material.

The coupler 204 may include one or more pieces of desiccant material 1140 located within the focus ring 2014 between seal 1126 and seal 1136 to absorb moisture that may advance through the seals 1126, 1136. FIG. 12 illustrates a partial cutaway view of the focus ring 214 with a number of pieces of desiccant material 1140A, 1140B, and 1140C. The desiccant material 1140A-C may be wrapped in a wrapping material 1142 (e.g., paper, or a porous polymer fabric) that can help retain loose particles of desiccant. The desiccant material 1140A-C may be located in pockets 1144 formed in the focus ring 214. The wrapped desiccant material 1140A-C may be held in place in their respective pockets 1144 by a band 1146 (e.g., a steel band).

Returning to FIG. 11, another location where fogging can occur is on the external side of the window 510 and/or the external side of a proximal window 1150 of the eyepiece 300 due to moisture present in the space between the window 510 and the proximal window 1150. To limit trapping of moisture in this space, coupler 204 includes vents 508 formed in the main body 401 that enable free exchange of air outside of the space. The focus ring 214 may be configured such that a relatively large gap 1152 is maintained for air to move into and out of the space between the eyepiece at the window 510.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A coupler for coupling an endoscope to a camera head, the coupler comprising:

a base configured to mount to the camera head and to receive an eyepiece of the endoscope;

a clamp for clamping the eyepiece in the base, the clamp configured to move laterally relative to a longitudinal axis of the coupler between a clamping position and non-clamping position;

at least one clamping arm rotatably connected to the clamp such that movement of the clamp from the non-clamping position to the clamping position causes the at least one clamping arm to rotate into engagement with the eyepiece; and a button for pressing by a user to move the clamp from the clamping position to the non-clamping position.

2. The coupler of claim 1, wherein the clamp is biased toward the clamping position, and the clamp extends from the button.

3. The coupler of claim 1, wherein the button is biased by at least one spring located beneath the button.

4. The coupler of claim 1, comprising a front cover attached to the base, wherein the clamp is retained between the front cover and the base.

5. The coupler of claim 1, wherein the clamp is configured to engage the eyepiece at two or more spaced apart locations.

6. The coupler of claim 5, wherein the clamp comprises at least two arms, an end portion of each respective arm configured to engage the eyepiece at different ones of the two or more spaced apart locations.

7. The coupler of claim 5, wherein the clamp comprises a semicircular portion configured to engages the eyepiece at the two or more spaced apart locations.

8. The coupler of claim 1, wherein the at least one clamping arm comprises first and second clamping arms.

9. The coupler of claim 1, wherein the base comprises a recess for receiving the eyepiece, wherein the clamp and the at least one clamping arm are positioned outwardly of the recess when the clamp is in the non-clamping position.

10. The coupler of claim 1, comprising a focus ring rotatably mounted to the base and configured to translate at least one optical component of the coupler to adjust a focus of the coupler, a plurality of seals that seal between the focus ring and a main body of the base, and at least one desiccant located within one or more pockets of the focus ring.

11. The coupler of claim 10, wherein the at least one desiccant is retained within the one or more pockets by a band.

12. The coupler of claim 10, wherein the focus ring includes a groove that receives a rib of the main body of the base forming a pathway to an associated seal of the plurality of seals that includes a plurality of ninety degree turns.

13. A method of coupling an endoscope to a camera head, the method comprising:

pressing a button of a coupler mounted to the camera head, the coupler further comprising:

a base mounted to the camera head and configured to receive an eyepiece of the endoscope;

a clamp for clamping the eyepiece in the base; and at least one clamping arm rotatably connected to the clamp;

wherein pressing the button causes the causing a clamp of the coupler to move laterally relative to a longitudinal axis of the coupler away from a clamping position to a non-clamping position;

positioning the eyepiece of the endoscope at least partially in the coupler; and releasing the button, causing the clamp to move laterally from the non-clamping position to the clamping position and engage the eyepiece such that the eyepiece is retained in the coupler, wherein when the clamp moves laterally from the non-clamping position to the clamping position, the at least one clamping arm rotates relative to the clamp into engagement with the eyepiece.

14. The method of claim 13, wherein the clamp is biased toward the clamping position.

15. The method of claim 13, wherein the at least one clamping arm comprises a pin that moves in a slot of a base of the coupler when the at least one clamping arm rotates relative to the clamp.

16. The method of claim 13, wherein the clamp in the clamping position engages the eyepiece at two or more spaced apart locations.

17. The method of claim 16, wherein a first arm of the clamp engages the eyepiece at a first one of the two or more spaced apart locations and a second arm of the clamp engages the eyepiece at a second one of the two or more spaced apart locations.

18. The method of claim 16, wherein the clamp comprises a semicircular portion that engages the eyepiece at the two or more spaced apart locations.

19. A system comprising:

a camera head; and a coupler comprising:

a base mounted to the camera head and configured to receive an eyepiece of an endoscope, a clamp for clamping the eyepiece in the base, the clamp configured to move laterally relative to a longitudinal axis of the coupler between a clamping position and non-clamping position, at least one clamping arm rotatably connected to the clamp such that movement of the clamp from the non-clamping position to the clamping position causes the at least one clamping arm to rotate into engagement with the eyepiece, and a button for pressing by a user to move the clamp from the clamping position to the non-clamping position.

* * * * *